United States Patent [19]
Chitnis et al.

[11] Patent Number: 5,994,550
[45] Date of Patent: Nov. 30, 1999

[54] PYRIDINE/PICOLINE PRODUCTION PROCESS

[75] Inventors: Girish K. Chitnis, Chadds Ford, Pa.; Jocelyn A. Kowalski, Sewell, N.J.; John P. Mc Williams, Woodbury, N.J.; Yung-Yang Huang, Voorhees, N.J.; Chaya R. Venkat, Princeton, N.J.

[73] Assignee: Mobil Oil Corporation, Fairfax, Va.

[21] Appl. No.: 09/223,658

[22] Filed: Dec. 30, 1998

[51] Int. Cl.⁶ .................. C07D 213/08; C07D 213/09; C07D 213/10
[52] U.S. Cl. ............................ 546/251; 546/251
[58] Field of Search .................... 546/250, 251

[56] References Cited

U.S. PATENT DOCUMENTS

| | | | |
|---|---|---|---|
| 2,807,618 | 9/1957 | Cislak et al. | 546/251 |
| 3,650,988 | 3/1972 | Magee, Jr. et al. | 252/451 |
| 3,932,431 | 1/1976 | Walter | 546/275.1 |
| 3,946,020 | 3/1976 | Minato et al. | 546/251 |
| 4,220,783 | 9/1980 | Chang et al. | 546/251 |
| 4,247,420 | 1/1981 | Dumoulin et al. | 252/453 |
| 4,356,338 | 10/1982 | Young | 585/407 |
| 4,380,685 | 4/1983 | Chu | 585/466 |
| 4,554,394 | 11/1985 | Forbus et al. | 585/474 |
| 4,556,447 | 12/1985 | Bradley et al. | 156/578 |
| 4,675,410 | 6/1987 | Feitler et al. | 546/251 |
| 5,013,843 | 5/1991 | Feitler et al. | 546/251 |
| 5,110,776 | 5/1992 | Chitnis et al. | 502/64 |
| 5,231,064 | 7/1993 | Absil et al. | 502/68 |
| 5,348,643 | 9/1994 | Absil et al. | 208/114 |

OTHER PUBLICATIONS

Advances in Catalysis, 18: 344 (1968).

Microporous and Mesoporous Materials, vol. 21, pp. 447–451 (1998).

*Primary Examiner*—Alan L. Rotman
*Attorney, Agent, or Firm*—Peter W. Roberts; Malcolm D. Keen

[57] ABSTRACT

A process is provided for producing pyridine and/or alkylpyridine compounds comprising reacting a feedstream of ammonia and at least one $C_{1-5}$ carbonyl reactant under conversion conditions and in the presence of a phosphorus-modified molecular sieve containing catalyst to produce a product stream having a pyridine and/or a pyridine based compound selected from alkylpyridines or polyalkylpyridines. The catalyst has improved attrition resistance without affecting catalyst activity or selectivity.

10 Claims, No Drawings

PYRIDINE/PICOLINE PRODUCTION PROCESS

FIELD OF THE INVENTION

This invention relates to an improved process for producing pyridine and/or picoline or other alkylated pyridines using a phosphorus containing catalyst having improved attrition resistance.

BACKGROUND OF THE INVENTION

Pyridine is an important intermediate in the manufacture of agricultural chemicals, e.g., herbicides and pesticides, and pharmaceuticals, and is also useful as a solvent in the polymer and textile industries. Important derivatives of pyridine include, for example, nicotinic acid and nicotinamide (vitamins essential for human health), chlorpheniramine (an antihistamine), cetylpyridinium (a germicide and antiseptic), isoniazid (an important antitubercular drug), and Paraquat® (a herbicide).

Pyridines having one methyl group attached to the ring structure are called methylpyridines or picolines, and include 2- or α-picoline, 3- or β-picoline, and 4- or γ-picoline.

Pyridine and picolines can be obtained as by-products of the coal tar industry or coke manufacture. However, pyridine is found in only small amounts in coal tar, and a preferred method of obtaining pyridine is by chemical synthesis. Chemical synthesis typically relies on a catalytic gaseous reaction (condensation) between ammonia (or amines) and carbonyl compounds such as aldehydes or ketones. However, these chemical synthesis methods have historically suffered from disadvantages of low yields and poor selectivity, and short operation cycle and catalyst lifetime.

The term "base synthesis" is known and used in the field of pyridine chemistry to identify synthetic processes by which bases of pyridine and its alkylated derivatives are prepared by reacting aldehydes and/or ketones with ammonia in the gas phase using a heterogeneous catalyst. For example, the reaction of acetaldehyde with ammonia in the presence of heterogeneous catalysts at 350 to 550° C. yields 2- and 4-methylpyridines (α- and γ-picolines). As another example, acetaldehyde and formaldehyde, can be reacted with ammonia to yield pyridine and 3-methylpyridine. Such pyridine synthesis methods are described, for example, in U.S. Pat. No. 4,675,410 to Feitler and U.S. Pat. No. 4,220,783 to Chang et al.

Reaction of acetaldehyde or certain other low molecular weight aldehydes and ammonia either in the absence or presence of methanol and/or formaldehyde to yield pyridine and alkyl derivatives thereof has been carried out in the presence of amorphous silica-alumina composites containing various promoters. See, for example, U.S. Pat. Nos. 2,807,618 and 3,946,020. The yields of desired products using the latter catalysts have been poor. Alkylpyridines have also been synthesized, as reported in Advances in Catalysis, 18:344 (1968), by passing gaseous acetaldehyde and ammonia over the crystalline aluminosilicates NaX and H-mordenite. While initial conversion utilizing these materials as catalysts was high, catalyst deactivation by coking was rapid, providing a commercially unattractive system, characterized by poor catalytic stability.

Synthetic crystalline zeolites having an intermediate pore size as measured by the Constraint Index of the zeolite being between 1 and 12, e.g., ZSM-5, have been found to provide commercially useful yields and product selectivities. U.S. Pat. No. 4,220,783 was pioneer in this discovery, teaching synthesis of pyridine and alkylpyridines by reacting ammonia and a carbonyl reactant which is an aldehyde containing 2 to 4 carbon atoms, a ketone containing 3 to 5 carbon atoms or mixtures of said aldehydes and/or ketones under effective conditions in the presence of a catalyst comprising a crystalline aluminosilicate zeolite having been ion exchanged with cadmium and having a silica to alumina ratio of at least 12, and a Constraint Index within the range of 1 to 12.

Use of a ZSM-5 catalyst component in a fluidized or otherwise movable bed reactor is taught in U.S. Pat. No. 4,675,410. U.S. Pat. No. 4,886,179 teaches synthesis of pyridine by reaction of ammonia and a carbonyl compound, preferably with added hydrogen, over catalyst comprising a crystalline aluminosilicate zeolite which has been ion exchanged with a Group VIII metal of the Periodic Table. The crystalline aluminosilicate zeolite has a silica to alumina mole ratio of at least 15, preferably 30 to 200, a Constraint Index of from 4 to 12, e.g., ZSM-5, and the process provides a high and selective yield of pyridine.

U.S. Pat. No. 5,013,843 teaches addition of a third aldehyde or ketone to a binary mixture of aldehydes and/or ketones used in preparing mixtures of pyridine and alkyl-substituted pyridines in large scale continuous processes. In a preferred system, propionaldehyde is added to a binary mixture of acetaldehyde and formaldehyde to produce beta-pyridine and pyridine. The catalyst for this process is a crystalline aluminosilicate zeolite in the acidic form having a Constraint Index of from 1 to 12, e.g., ZSM-5.

The use of a ZSM-5 catalyst modified with metals such as thallium, lead, or cobalt has been shown to increase the selectivity of pyridine by Shimizu, et al. in *Microporous and Mesoporous Materials*, Vol. 21, pp 447–451 (1998).

However, despite recent advances, existing processes for producing pyridine and picolines suffer from the disadvantage that although commercially acceptable, catalyst losses due to poor mechanical strength of the catalytic medium result in high operating costs, and an attrition resistant catalyst for manufacturing pyridine, picoline or other alkylated pyridines would be desirable.

U.S. Pat. No. 5,110,776 discloses the use of small amounts of phosphate treated zeolite catalysts, for example ZSM-5, as additives in fluid catalytic cracking (FCC) processes to improve octane yield by producing olefins. The phosphate treated catalyst, in addition to having improved catalytic properties, also has improved attrition resistance. The use of phosphorus modified ZSM-5 fluid bed catalysts as additive catalysts to improve the olefin yield in FCC is also described in U.S. Pat. No. 5,389,232 and in U.S. Pat. No. 5,472,594.

U.S. Pat. No. 4,380,685 relates to a process for para-selective aromatics alkylation, including the methylation of toluene, over a zeolite, such as ZSM-5, which has a constraint index of 1–12 and which has been combined with phosphorus and a metal selected from iron and cobalt. U.S. Pat. No. 4,554,394 discloses the use of phosphorus-treated zeolite catalysts for enhancing para-selectivity in aromatics conversion processes.

Combining phosphorus with a molecular sieve, as well as steaming, have been disclosed as useful to effect controlled reduction in diffusivity and micropore volume and enhance the selective production of para-xylene by toluene methylation in International Publication Number WO 98/14415.

The use of a phosphate modified amorphous catalytic material to improve selectivity to 2-picoline and overall yield is disclosed in U.S. Pat. No. 3,932,431 to Minato et al.

In light of the aforementioned catalytic effect of phosphorus, it is quite remarkable that the inventors have discovered phosphorus treated molecular sieve materials used in processes for producing pyridine and/or picoline or other alkylated pyridines have minimal or no effect on the catalytic properties of the reaction, yet still exhibit improved mechanical properties.

SUMMARY OF THE INVENTION

Accordingly the invention resides in an improved process for producing pyridine or picoline or other alkylated pyridines or combinations thereof using a catalyst having improved attrition resistance properties comprising reacting a feedstream comprising ammonia and at least one $C_{1-5}$ carbonyl reactant under conversion conditions and in the presence of an attrition resistant molecular sieve catalyst comprising phosphorus to produce a product stream comprising pyridine, picoline, another monoalkylpyridine or a polyalkylpyridine, or a combination thereof. The molecular sieve is selected from ZSM-5, ZSM-11, ZSM-12, ZSM-22, ZSM-23, ZSM-35, ZSM-48, ZSM-57, ZSM-58, MCM-22, MCM-36, MCM-49, MCM-56, SAPO-5, SAPO-11, SSZ-25, SSZ-31, SSZ-33, SSZ-35, SSZ-36, SSZ-37, SSZ-41, SSZ-42, ferrierite, zeolite Beta, zeolite X, and zeolite Y. ZSM-5 is preferred. The weight percent phosphorus on an elemental basis in the molecular sieve catalyst is in the range of 0.1 to 10.0, preferably 1.0 to 5.0. The attrition resistance is less than about 20, preferably 10 or less, when measured by the Davison Index attrition test (DI@1000), wherein the catalyst has been pretreated by calcination at 1000° F. for one hour prior to testing.

The carbonyl reactant used in the reaction is a hydrocarbon compound containing 1 to 5 carbon atoms and at least one carbonyl moiety. The carbonyl reactant taking part in the catalytic reaction described herein may be formaldehyde, an aldehyde containing 2 to 4 carbon atoms, a ketone containing 3 to 5 carbon atoms or mixtures thereof. Representative reactant aldehydes include acetaldehyde, propionaldehyde, acrolein, butyraldehyde, and crotonaldehyde. Representative reactant ketones include acetone, methyl ethyl ketone, diethyl ketone, and methyl propyl ketone. The carbonyl reactant can be present as a solution in water, e.g., formalin which is a solution of formaldehyde in water, with a small amount of methanol to aid solubility. Methanol or other alcohols may also be added to the carbonyl reactant(s) feed as a co-solvent processing aid. Methanol may also be used in the regeneration step aeration gas as is disclosed by Shimizu, et al. in *Microporous and Mesoporous Materials*, Vol. 21, pp 447–451 (1998).

The carbonyl reactant may comprise a mixture of two or more carbonyl compounds. If a mixture is used, each carbonyl component in the mixture is preferably present in a predetermined amount relative to the other carbonyl components. For example, when the at least one carbonyl reactant is a mixture of formaldehyde and acetaldehyde, the two components are preferably present in a formaldehyde/acetaldehyde mole ratio of from 0.2 to 1.0, more preferably from 0.4 to 0.8. Alternatively, mixtures of acetaldehyde and acrolein will typically have an acetaldehyde/acrolein mole ratio of from about 0.7 to about 1.25. Other mixtures of carbonyl reactants can be similarly formulated to selectively control the product of the reaction. Preferably the carbonyl reactant comprises a mixture of formaldehyde and acetaldehyde and the primary product of the reaction is pyridine and β-picoline.

The mole ratio of ammonia to carbonyl reactant ($NH_3$/CO) in the reaction mixture employed will generally be between 0.5 and 30, preferably between 0.5 and 10, and more preferably between 1 and 5.

Hydrogen gas ($H_2$) may, if desired, be added to the reaction, e.g., at the rate of from 0 (no added hydrogen) to an $H_2$/carbonyl reactant ($H_2$/CO) mole ratio of 5.0, preferably from 0.1 to 1.0.

The reaction conditions for performing the reaction between the ammonia and the at least one carbonyl compound include a temperature of 285° C. to 650° C., preferably 340° C. to 550° C.; a pressure of 20 kPa to 10,000 kPa (0.2 to 100 atm), preferably 80 kPa to 1,000 kPa (0.8 to 10 atm); and a weight hourly space velocity (WHSV) of 0.1 to 100, preferably 1 to 10.

Catalyst System

The reaction is performed over a catalyst comprising a molecular sieve and phosphorus. The phosphorus may be incorporated into the molecular sieve material, the binder material, or both the molecular sieve and the binder material. Preferred molecular sieve catalysts are crystalline and are those having an intermediate pore size characterized by a Constraint Index 1 to 12. Constraint Index and the method by which it is determined are described in U.S. Pat. No. 4,016,218. Examples of suitable intermediate pore size molecular sieves include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,447); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780).

Other useful catalyst materials include MCM-22 (U.S. Pat. No. 4,954,325), MCM-36 (U.S. Pat. No. 5,250,277), MCM-49 (U.S. Pat. No. 5,236,575) and MCM-56 (U.S. Pat. No. 5,362,697). SAPO-5, SAPO-11, SSZ-25, SSZ-31, SSZ-33, SSZ-35, SSZ-36, SSZ-37, SSZ41, SSZ-42, ferrierite, zeolite X, zeolite Y, and zeolite Beta are also examples of molecular sieve materials that can also be used according to the invention.

To effect the desired increase in attrition resistance, it is desirable to combine the molecular sieve material and/or the binder material with at least one oxide modifier, preferably selected from oxides of the elements of Groups IIA, IIIA, IIIB, IVA, IVB, VA and VIA of the Periodic Table (IUPAC version). Most preferably, said at least one oxide modifier is selected from oxides of titanium, zirconium, boron, magnesium, calcium, lanthanum and most preferably phosphorus. In some cases, it may be desirable to combine the molecular sieve material with more than one oxide modifier, for example a combination of phosphorus with boron. The total amount of oxide modifier present in the catalyst, as measured on an elemental basis, may be between about 0.1 and about 10 wt. %, and preferably is between about 1.0 and about 5 wt. %, based on the weight of the final catalyst.

The improved attrition resistance of the catalyst of the invention comprising a molecular sieve and phosphorus is measured by the Davison Index attrition test. The Davison Index attrition test is described generally in U.S. Pat. Nos. 3,650,988 to Magee, Jr. et al and 4,247,420 to Dumoulin et al., which are incorporated by reference herein for such general disclosure.

For the catalyst system of the present invention, the Davison Index attrition test is performed for one hour, at twenty-one liters/minute air flow with a jet cup obtained from Grace Davison. In addition, the catalyst of the present invention is pretreated (calcined) at 1000° F. prior to initiating the specific one hour duration Davison Index attrition test of the present invention (DI@1000).

Where the modifier includes phosphorus, incorporation of modifier in the catalyst of the invention is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the molecular sieve material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

After contacting with the phosphorus-containing compound, the molecular sieve material may be dried and calcined to convert the phosphorus to an oxide form. Calcination can be carried out in an inert atmosphere or in the presence of oxygen, for example, in air at a temperature of about 150 to 750° C., preferably about 400 to 600° C., for at least 15 minutes, preferably ½–3 hours.

Similar techniques known in the art can be used to incorporate other modifying oxides into the catalyst of the invention.

Representative phosphorus-containing compounds which may be used to incorporate a phosphorus oxide modifier into the catalyst of the invention include derivatives of groups represented by PX3, RPX2, R2PX, R3P, X3PO, (XO)3PO, (XO)3P, R3P=O, R3P=S, RPO2, RPS2, RP(O)(OX)2, RP(S)(SX)2, R2P(O)OX, R2P(S)SX, RP(OX)2, RP(SX)2, ROP(OX)2, RSP(SX)2, (RS)2PSP(SR)2, and (RO)2POP(OR)2, where R is an alkyl or aryl, such as phenyl radical, and X is hydrogen, R, or halide. These compounds include primary, RPH2, secondary, R2PH, and tertiary, R3P, phosphines such as butyl phosphine, the tertiary phosphine oxides, R3PO, such as tributyl phosphine oxide, the tertiary phosphine sulfides, R3PS, the primary, RP(O)(OX)2, and secondary, R2P(O)OX, phosphonic acids such as benzene phosphonic acid, the corresponding sulfur derivatives such as RP(S)(SX)2 and R2P(S)SX, the esters of the phosphonic acids such as dialkyl phosphonate, (RO)2P(O)H, dialkyl alkyl phosphonates, (RO)2P(O)R, and alkyl dialkylphosphinates, (RO)P(O)R2; phosphinous acids, R2POX, such as diethylphosphinous acid, primary, (RO)P(OX)2, secondary, (RO)2POX and tertiary, (RO)3P, phosphites, and esters thereof such as the monopropyl ester, alkyl dialkylphosphinites, (RO)PR2, and dialkyl alkyphosphinite, (RO)2PR, esters. Corresponding sulfur derivatives may also be employed including (RS)2P(S)H, (RS)2P(S)R, (RS)P(S)R2, R2PSX, (RS)P(SX)2, (RS)2PSX, (RS)3P, (RS)PR2, and (RS)2PR. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, (RO)PCl2, dialkylphosphorochloridites, (RO)2PCl dialkylphosphinochloroidites, R2PCl, alkyl alkylphosphonochloridates, (RO)(R)P(O)Cl, dialkyl phosphinochloridates, R2P(O)Cl, and RP(O)Cl2. Applicable corresponding sulfur derivatives include (RS)PCl2, (RS)2PCl, (RS)(R)P(S)Cl, and R2P(S)Cl.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-P2O5 reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

The molecular sieve material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin. Said materials, i.e., clays, oxides, etc., function as binders for the catalyst.

Naturally occurring clays that can be composited with the molecular sieve include those of the montmorillonite and kaolin families, which families include the subbentonites and the kaolins commonly known as Dixie, McNamee, Georgia, and Florida clays, or others in which the main mineral constituent is halloysite, kaolinite, dickite, nacrite, or anauxite. Suitable clay materials include, by way of example, bentonite and kieselguhr. Such clays can be used in the raw state as originally mined or initially subjected to calcination, acid treatment, or chemical modification.

The relative proportion of suitable crystalline molecular sieve to the total composition of catalyst and binder or support may be from about 1.0 wt % to about 90 wt %, preferably from about 5.0 wt % to about 70 wt %, and more preferably from about 20wt % to about 60wt %, of the composition.

A hydrogenation-dehydrogenation functional metal can be incorporated into the catalyst of the invention. The amount of the functional metal is suitably from 0.001 wt % to 10 wt %, preferably from 0.005 wt % to 5 wt %, more preferably from 0.02 wt % to 2 wt %, based on the total weight of the modified catalyst. Examples of suitable hydrogenation-dehydrogenation metals include Group 8, 9, and 10 metals (i.e., Pt, Pd, Ir, Rh, Os, Ru, Ni, Co, and Fe), Group 7 metals (i.e., Mn, Tc, and Re), Group 6 metals (i.e., Cr, Mo, and W), Group 15 metals (i.e., Sb and Bi), Group 14 metals (i.e., Sn and Pb), Group 13 metals (i.e., Ga and In), Group 11 metals (i.e., Cu, Ag, and Au), and Group 12 metals (i.e., Zn, Cd, and Hg). Noble metals (i.e., Pt, Pd, Ir, Rh, Os, Re, Ru, Mo, and W) are preferred.

COMPARATIVE EXAMPLE 1

A conventional pyridine/picoline production catalyst was made by spray drying and calcining a slurry to yield a catalyst comprising ZSM-5 in a silica-alumina-clay matrix. The weight ratio of zeolite to binder was 35:65 and the silica:alumina ratio of the ZSM-5 zeolite was 55:1.

EXAMPLE 2

The catalyst preparation procedure of Comparative Example 1 was duplicated, with the addition of 1 part by weight of phosphoric acid to 10.3 parts by weight of the catalyst mixture to yield a 2.8% weight percent phosphorus catalyst (on an elemental basis) comprising ZSM-5 in a silica-alumina-clay matrix.

EXAMPLE 3

The catalysts of Comparative Example 1 and Example 2 were evaluated using the Davison Index attrition test described above, i.e DI@1000. The phosphorus improved the attrition resistance of the catalyst of Comparative Example 1 from 25 to 10, the value for Example 2, the phosphorus modified catalyst. The lower value represents improved attrition resistance.

EXAMPLE 4

The catalysts of Comparative Example 1 and Example 2 were evaluated for catalytic performance. The data is shown below.

| Catalytic Performance for Production of Pyridine and Beta-Picoline | | |
| --- | --- | --- |
| | Catalyst of Comparative Example 1 | Catalyst of Example 2 |
| Test Conditions | | |
| Catalyst Charge, gm | 450 | 450 |
| Reactor Temp, ° C. | | |
| Reactor Average | 450 | 455 |
| Run Time, Hrs | 7 | 8 |
| Mass Balance Period, Hrs | 7 | 8 |
| Total Feed In, gms | 1342.35 | 1621.3 |
| Acetaldehyde | 384.42 | 464.55 |
| Formaldehyde | 249.85 | 301.71 |
| Water | 391.66 | 472.95 |
| Methanol | 33.76 | 40.77 |
| Ammonia | 282.66 | 341.3 |
| | Catalyst of Example 1 | Catalyst of Example 2 |
| Total Product Collected, gms | 1264.5 | 1525.0 |
| Unreacted aldehydes as HCHO | 14.16 | 17.08 |
| Ammonia + Alkyl amines | 173.86 | 217.0 |
| Pyridine | 172.35 | 206.0 |
| Alpha-picoline | 0.51 | Nil |
| Beta-Picoline + Gamma-Picoline | 82.95 | 98.66 |
| Water | 682.32 | 819.23 |
| Heavy bases + neutral oils | 138.35 | 167.03 |
| % Carbon on Catalyst | 3.96 | 4.09 |
| % Mass Balance | 95.53 | 95.20 |
| Percent Molar Yield | | |
| Pyridine | 49.90 | 49.28 |
| Catalytic Performance for Production of Pyridine and Beta-Picoline | | |
| Beta-Picoline | 20.37 | 20.09 |
| TOTAL | 70.27 | 69.38 |
| Pyridine/Beta-Picoline (wt. Ratio) | 2.07 | 2.08 |

The results of Examples 3 & 4 show that while attrition resistance improved dramatically, quite remarkably, in view of its demonstrated catalytic activity, the addition of phosphorus had no impact on the catalytic performance as measured by the i) pyridine yield, ii) Beta-picoline yield and iii) the pyridine/Beta-picoline selectivity.

What is claimed is:

1. A process for producing pyridine and/or alkylpyridine compounds comprising reacting a feedstream comprising ammonia and at least one $C_{1-5}$ carbonyl reactant under conversion conditions and in the presence of a catalyst comprising a molecular sieve and phosphorus to produce a product stream comprising a pyridine and/or a pyridine based compound selected from alkylpyridines or polyalkylpyridines.

2. The process according to claim 1, wherein said conversion conditions comprise a temperature of 285° C. to 650° C. and a pressure of 20 kPa to 10,000 kPa (0.2 to 100 atm).

3. The process according to claim 1, wherein the molecular sieve is selected from ZSM-5, ZSM-11, ZSM-12, ZSM-22, ZSM-23, ZSM-35, ZSM-48, ZSM-57, ZSM-58, MCM-22, MCM-36, MCM-49, MCM-56, SAPO-5, SAPO-11, SSZ-25, SSZ-31, SSZ-33, SSZ-35, SSZ-36, SSZ-37, SSZ-41, SSZ-42, ferrierite, zeolite Beta, zeolite X, and zeolite Y.

4. The process according to claim 3, wherein the molecular sieve is ZSM-5.

5. The process according to claim 4, wherein the weight percent phosphorus in the molecular sieve catalyst is in the range of 0.1 to 10.

6. The process according to claim 1, wherein the at least one carbonyl reactant comprises acetaldehyde and formaldehyde.

7. The process according to claim 5 wherein the attrition resistance is less than about 20, when measured by DI@1000.

8. The process according to claim 5 wherein the attrition resistance is 10 or less, when measured by DI@1000.

9. The process according to claim 1 wherein said phosphorus is incorporated into said molecular sieve.

10. The process according to claim 1 wherein said molecular sieve is crystalline.

* * * * *